United States Patent [19]

Rice et al.

[11] Patent Number: 4,659,681

[45] Date of Patent: Apr. 21, 1987

[54] PROMOTED IRON-CARBON-BASED CATALYSTS PRODUCED IN THE PRESENCE LASER RADIATION

[75] Inventors: Gary W. Rice, Whitehouse Station; Rocco A. Fiato, Scotch Plains; Stuart L. Soled, Pittstown, all of N.J.

[73] Assignee: Exxon Research and Engineering Company, Florham Park, N.J.

[21] Appl. No.: 735,768

[22] Filed: May 20, 1985

[51] Int. Cl.$^4$ .................. B01J 37/34; B01J 27/22
[52] U.S. Cl. .................. 502/5; 204/157.41; 502/177; 502/183; 502/184; 502/185; 518/717; 518/721
[58] Field of Search .............. 502/5, 522, 177–179, 502/183–185; 423/439; 204/157.1 R, 157.1 H, 157.41; 427/53.1

[56] References Cited

U.S. PATENT DOCUMENTS

| | | | |
|---|---|---|---|
| 2,535,042 | 12/1950 | Cohn et al. | 502/177 |
| 2,608,535 | 8/1952 | Gillespie | 502/184 |
| 3,494,738 | 2/1970 | Gray et al. | 423/439 |
| 3,885,023 | 5/1975 | Gray et al. | 423/439 |
| 4,468,474 | 8/1984 | Gupta et al. | 502/5 |

FOREIGN PATENT DOCUMENTS 731295 2/1943 Fed. Rep. of Germany .

OTHER PUBLICATIONS

Brennstoff–Chem. 7, 97 (1926).
Hall et al., J. Soc. Chem. Ind. London 65, 128 (1946).
Weller, J. Am. Chem. Soc. 69, 2432 (1947).
Kummer et al., J. Am. Chem. Soc. 70, 3632 (1948).
Malan et al., Brennstoff–Chem, 42, 209–212 (1961).
SPIE 458, Appl. of Lasers to Industrial Chemistry, 131-139 (1984).
Catal. Rev.-Sci. Engr. 21, 1980 p. 225 (Kolbol, Rulek).
Gilbert, A. G., Sulzman, K.G.P., *J. Electrochem. Soc.*, 1974, 121, 832-834.

*Primary Examiner*—P. E. Konopka
*Attorney, Agent, or Firm*—E. Thomas Wheelock

[57] ABSTRACT

This invention relates to a promoted finely divided or supported iron carbide-based catalyst which is produced by a gas phase pyrolytic decomposition reaction driven by a laser and the use of such a catalyst to produce various heavier hydrocarbons from CO and $H_2$.

12 Claims, 1 Drawing Figure

Laser Synthesis Reactor

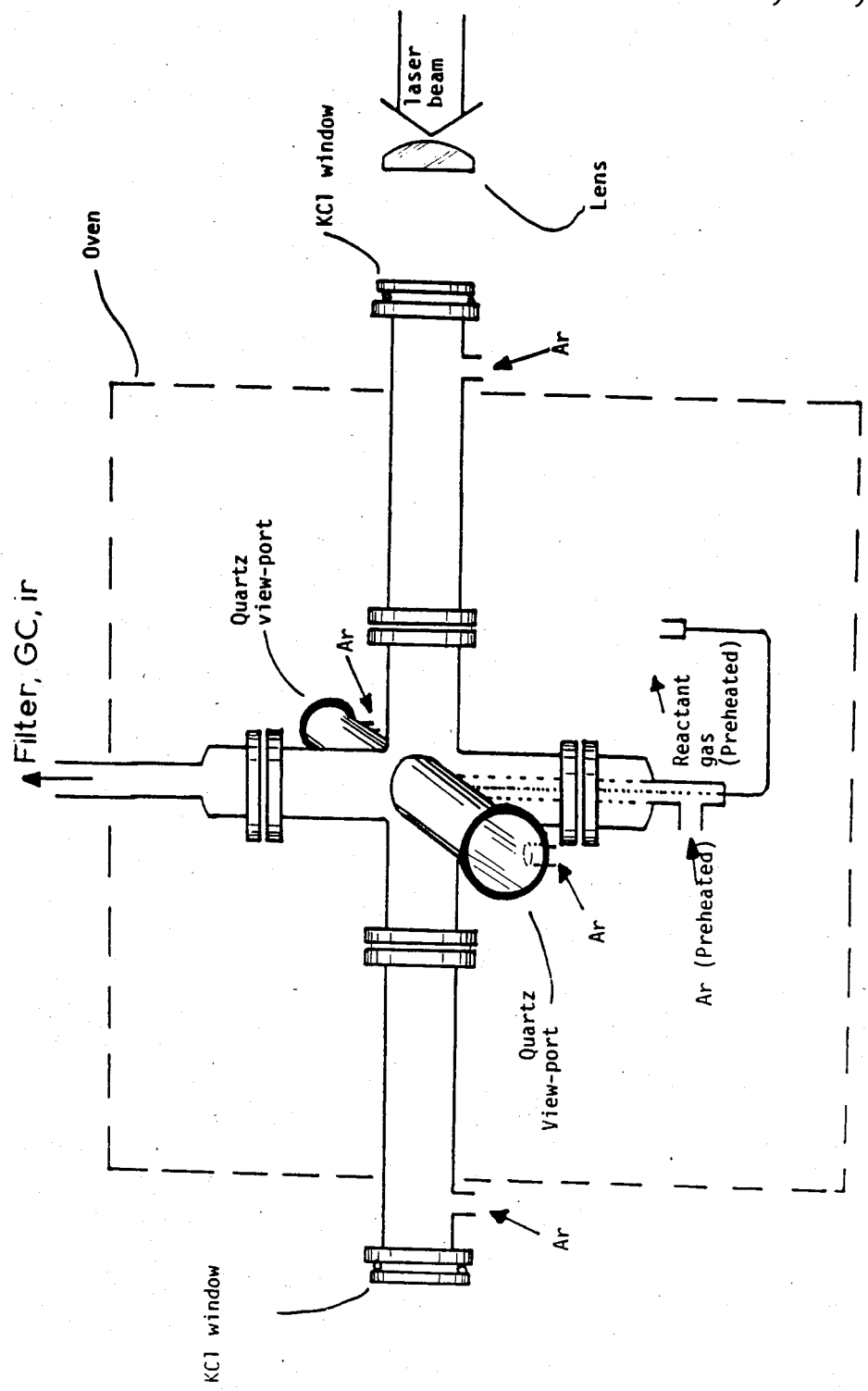
Figure 1. Laser Synthesis Reactor

PROMOTED IRON-CARBON-BASED CATALYSTS PRODUCED IN THE PRESENCE LASER RADIATION

FIELD OF THE INVENTION

This invention relates to a promoted finely divided or supported iron carbide-based catalyst which is produced by a gas phase pyrolytic decomposition reaction driven by a laser and the use of such a catalyst to produce various heavier hydrocarbons, typically paraffin waxes, from CO and $H_2$.

BACKGROUND OF THE INVENTION

The Fischer-Tropsch reaction involves the catalytic hydrogenation of carbon monoxide to produce a variety of products ranging in size and functionality from methane to higher alcohols. The methanation reaction was first described by Sabatier and Senderens in 1902. The later work of Fischer and Tropsch dealing with higher hydrocarbons was described in Brennstoff-Chem. 7, 97 (1926).

The reaction is highly exothermic and care must be taken to design reactors for adequate heat exchange capacity. Nevertheless, substantial research has been undertaken in the interim since the initial characterization of the reaction during the 1920's. The process is especially suitable for use when carbonaceous feedstocks of otherwise low economic value are available. For instance, the first major commercial use of the Fischer-Tropsch process was in Germany during the mid-30's. By the beginning of World War II, Germany was producing nearly 11,000 B/D of primary products using mainly the cobalt-based catalyst described by Fischer and Pichler (Ger. Pat. No. 731,295 issued Aug. 2, 1936). The feedstock was, in general, based on available coals.

Subsequently, a consortium of nine American companies designed and built a plant at Brownsville, Tex. based on an iron-based catalyst. The plant was completed in 1950 and had a design capacity of 50MMSCFD. Various economic and technical difficulties caused final shutdown of the plant in the late 50's.

A reasonably economic use of the process has been practiced in South Africa in the SASOL plants. These plants use an iron-based catalyst and produce gasoline and waxes by gasifying a somewhat low-grade coal to produce a synthesis gas for feed to the Fischer-Tropsch reactors.

Reseach continues in this area because of the potential for converting low value feedstocks into higher value products.

The chemistry of the Fischer-Tropsch reactions is, in a gross sense, quite simple. The overall reactions for the production of alkanes (No. 1), alkenes (No. 2) and alcohols (No. 3) are as follows:

1. 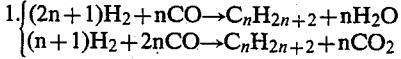
2. 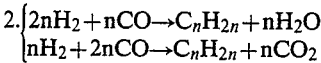
3. 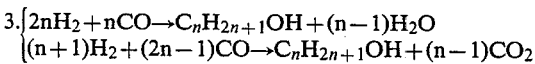

The types and amount of products obtained via such reactions are typically dependent upon the reaction conditions and choice of catalyst.

Few of the catalysts used in the past have been either very selective or very active. Those catalysts that were selective or active were uneconomic for other reasons, e.g., sensitivity to sulfur poisoning or used high cost catalytic metals such as ruthenium.

The catalyst of the present invention is iron/carbon-based. Because of the method of its preparation, the catalyst has high selectivity and/or conversion at reaction conditions considered to be quite moderate.

As noted above in the historical discussion, iron-bearing catalysts were among the first ever used in the Fischer-Tropsch reaction. Indeed, Fischer and Tropsch believed that carbides were an intermediate in the overall reaction. Later kinetics work suggested carbides could not be an intermediate in the process. Hall et al, J. Soc. Chem. Ind. London 65, 128 (1946); Weller, J. Am. Chem. Soc. 69, 2432 (1947) and; Kummer et al, J. Am. Chem. Soc. 70, 3632 (1948). However, the reduced metallic iron, as used in the Lurgi-Ruhrchemie fixed bed process, appears to change from the original $\alpha$-Fe phase to a mixture of $\alpha$-Fe, $Fe_3O_4$, FeC and $Fe_2C$ as conversion operations continue. See, Malan et al Brennstoff-Chem. 42, 209–212 (1961).

The present invention, as will be discussed below in greater detail, involves the use of a laser to pyrolize low valence iron-carbon bearing compounds to produce a fine particle iron-carbon containing catalyst. At least a portion of the catalyst is the iron carbide, cementite.

Others have described the use of iron-carbon containing catalysts produced by laser pyrolysis in Fischer-Tropsch reactions. The work of Gupta et al (in U.S. Pat. No. 4,468,474), issued Aug. 28, 1984 and in SPIE 458, Appl. of Lasers to Industrial Chemistry, 131–139 (1984)) shows the production of iron, carbon and silicon-containing catalysts by a laser and the catalysts' subsequent use in the Fischer-Tropsch process. Moderate activity and high $C_2$–$C_4$ olefin selectivity is asserted for the catalysts.

Applicants' catalysts contain substantially no silicon.

No known prior art is believed to show the use of the catalyst described below in the efficient production of heavy hydrocarbons.

SUMMARY OF THE INVENTION

This invention deals with the production of heavier hydrocarbons, typically paraffin waxes, by using an alkali or alkaline-earth promoted iron-carbon catalyst which is produced by pyrolyzing a volatile iron-carbon-containing-compound, optionally in the presence of an additional carbon containing compound, with a laser. The catalyst so-produced will have added to it an alkali or alkaline earth metal promoter in the amount of greater than about 2% by weight.

The invention involves those catalysts and processes using those catalysts in a Fischer-Tropsch reaction to produce heavy, i.e., $C_5^+$ or $C_{20}^+$, hydrocarbons from CO and $H_2$.

BRIEF DESCRIPTION OF THE DRAWINGS

The drawing is a schematic representation of the laboratory device used to prepare the inventive catalyst used in the Examples.

DESCRIPTION OF THE PREFERRED EMBODIMENTS

The catalyst used in the present invention is a finely divided catalyst composition comprising iron and carbon, at least a portion of which is the iron carbide cementite, which when mixed with an alkali or alkali earth promoter produces a product mixture having substantial $C_{20}{}^+$ alkanes (waxes) from CO and $H_2$.

The basic iron-carbon catalyst composition used in the instant invention is disclosed and claimed in a related case (C-1884) filed the same date as the instant application. The basic catalyst may be prepared by gas phase pyrolytic decomposition of a volatile organic iron-containing compound (optionally in the presence of an additional carbon source) in the presence of a laser emission under conditions of laser power absorption, reactant and/or diluent flow rate and pressure to produce finely divided iron-carbon containing catalyst particles.

The organic-iron-containing compounds generally are iron carbonyls. Compounds such as $Fe(CO)_5$, ferrocene, and iron acetylacetonate are all suitable; $Fe(CO)_5$ is especially preferred. The optional carbon source may act only as a diluent, depending upon reaction conditions, or may add a source of carbon to the pyrolysis reaction. The preferred carbon sources are short chain olefins such as ethylene. Obviously, at least one of the components must absorb the radiated laser energy.

The partial pressure of the organic-iron-containing compounds depends upon the total pressure of the reactor but may be in the range of 20 to 500 torr; the optional carbon source may be 20 to 500 torr and a diluent such as argon or other noble gas may be included to bring the overall system pressure to a total of 200 to 1000 torr.

By "finely divided" Fe-C catalyst particles is meant those having average diameters between 1 and 100 nm, preferably 10–50 nm. The materials usually have a BET surface area of 15 to 50 $m^2/gm$, preferably 20–35 $m^2/gm$. The iron-carbon catalyst is at least a major portion cementite, $Fe_3C$. The catalyst is a mixture of phases and, in addition to the cementite, includes $\alpha$ and $\gamma$ phase iron. The surface iron of the as-produced catalyst is carbidic. The $\alpha$ and $\gamma$-Fe phases appear to be embedded in the cementite. In some cases, the varying phases appear to be more than a simple physical mixture and may constitute a nonequilibrium mixture. A minimum amount of carbonaceous material is present on the exterior surface of the catalyst as a coating. The coating acts as a moderate passivating agent. No hydrogen pretreatment is needed to activate the as-produced base catalyst. The catalyst is not pyrophoric. The catalyst contains less than about 1.0% oxygen and is substantially bereft of silicon. Although the method of producing this catalyst is believed, of itself, to produce a catalyst which is unique, the catalyst desirably contains no more than about 20% total carbon, preferably no more than about 12% total carbon, and most desirably between about 8% and 12% total carbon. Directionally, the higher the percentage of excess matrix carbon, the lower the amount of $C_{10}$ olefins produced.

The catalyst which has been found to be optimum for the preparation of the desired heavier hydrocarbons contains at least 2% alkali or alkaline earth metal, preferably from 2% to 10% by weight.

The laser used is preferably a continuous wave (cw) type capable of producing a flux of about 200 to 10,000 $W/cm^2$ in the reaction zone and further capable of resonant adsorption with a substance in the reaction zone. A $CO_2$ laser of adequate size is desirable. The residence time of the reactants in the laser beam zone should be between 1 and 60 ms. The quench rate for the products leaving the zone should be such that the total time the reactant/products are at the elevated temperature is 0.15 seconds or less. Quenching may be provided mainly by radiative energy loss from the reaction products.

It is to be understood that the reactor pressures and gas flow rates described herein are not critical to the synthesis of the base catalyst, but are merely convenient for the particular reactor design employed. The only requirements are than the operating conditions be such that the time scale of the reaction be short enough to prevent deposition of excess carbon on the solid particles produced in the reaction, and that temperatures sufficient to drive the reaction be reached. Depending upon the power of the particular laser used to drive the reaction and the design of the particular reactor used to conduct the synthesis, a wide range of reactor pressures and gas flow rates will allow preparation of the catalyst.

By changing the reaction conditions, it is possible to obtain other products from the same reactants. For example, increasing the $Fe(CO)_5:C_2H_4$ ratio to 1:4 while maintaining the same laser power yields a product which is substantially all free iron and pyrophoric. Decreasing the residence time of the reactants in the laser beam has substantially the same effect. Similarly, increasing the laser power, or otherwise raising the reaction temperature, increases the carbon content of the product by continued decomposition of $C_2H_4$ after the $Fe(CO)_5$ is depleted. An increase in reaction time would have a similar effect.

The iron-carbon catalyst particles may be used as-is to produce olefins; e.g., in an appropriate slurry reactor, or may be supported in one fashion or another as known in the art. The catalyst may be integrated with known supports to produce a larger catalyst matrix which may be handled with more ease.

Promoters such as alkali metals, preferably potassium, or alkaline earth metals, such as magnesium, may be added using known methods. For instance, up to 10% potassium, preferably 2%, may be added to the as-produced Fe-C catalyst by impregnation with an aqueous solution of a potassium salt such as potassium carbonate. More difficultly soluble materials may be ground and mulled with the as-produced Fe-C catalyst prior to compaction step such as pilling, tabletting or extruding.

Of course, for certain applications the iron carbide catalytic material may be placed on a refractory support such as alumina, silica, mullite, diatomaceous earth, silica-alumina co-mixtures or other materials known to provide high surface area.

The process for conversion of $CO/H_2$ to the various hydrocarbon products using the catalyst discussed above may be a fixed bed or preferably a slurry process. In the slurry process, the catalyst is suspended in a liquid hydrocarbon and the $CO/H_2$ mixture forced through the catalyst slurry allowing good contact between the $CO/H_2$ and the catalyst to initiate and maintain the hydrocarbon synthesis process. The slurry process is described in detail in such articles as Catal. Rev.—Sci. Engr., 21, 1980, pg. 225 (Kolbol, Rulek).

Advantages of a slurry process over that of a fixed bed process include better control of the exothermic heat produced in the Fischer-Tropsch process during the reaction and better control over catalyst activity maintenance by allowing continuous recycle, recovery, and rejuvenation procedures to be implemented. The slurry process can be operated in a batch or in a continuous cycle, and in the continuous cycle, the entire slurry can be circulated in the system allowing for better control of the primary products residence time in the reaction zone.

The slurry liquid used in the process is a liquid at the reaction temperature, should be chemically inert under the reaction conditions and should be a relatively good solvent for $CO/H_2$ and possess good slurrying and dispersing properties for the finely divided catalyst. Representative classes of organic liquids which can be utilized are high boiling paraffins, aromatic hydrocarbons, ethers, amines, or mixtures thereof. The high boiling paraffins include $C_{10}$–$C_{50}$ linear or branched paraffinic hydrocarbons; the aromatic hydrocarbons include $C_7$–$C_{20}$ single ring and multi- and fused ring aromatic hydrocarbons; the ethers include aromatic ethers and substituted aromatic ethers where the ether oxygen is sterically hindered from being hydrogenated; the amines include long chain amines which can be primary, secondary, and tertiary amines, wherein primary amines preferably contain at least a $C_{12}$ alkyl group in length, secondary amines preferably contain at least two alkyl groups being $C_7$ or greater in length, and tertiary amines preferably contain at least three alkyl groups being $C_6$ or higher in length. Representative examples of specific liquid slurry solvents useful are dodecane, tetradecane, hexadecane, octadecane, cosane, tetracosane, octacosane, dotriacontane, hexatritacosane, tetracontane, tetratetracontane, toluene, o-, m-, and p-xylene, mesitylene, $C_1$–$C_{12}$ mono- and multi-alkyl substituted benzenes, dodecylbenzene, naphthalene, anthracene, biphenyl, diphenylether, dodecylamine, di-nonylamine, trioctylamine, and the like. Preferred liquid hydrocarbon slurry solvent is octacosane or hexadecane.

The amount of catalyst used in the liquid hydrocarbon slurry solvent is generally about 10 to 60 g. of dry catalyst per 500 g. slurry liquid. Preferably about 30 to 50 g. dry catalyst per 500 g. slurry liquid slurry is utilized, being in about a respective 5:1 to 10:1 weight ratio.

The slurry system, comprised of the slurry liquid and finally divided catalyst, is generally stirred to promote good dispersion during the pretreatment in the process to avoid catalyst settling and to eliminate mass transport limitations between the gas and liquid phases.

The operating conditions for this process are generally as found below.

| | Fixed Bed | Slurry |
|---|---|---|
| T °C. | 200–250 | 200–250 |
| (pref.) | 220–240 | 220–240 |
| Press. (psig) | 50–500 | 50–500 |
| (pref.) | 150–500 | 150–500 |
| $H_2/CO$ | 0.5–9:1 | 0.5–9:1 |
| (pref.) | 1.8–2.5:1 | 1.8–2.5:1 |
| SHSV (volume fresh gas/ volume catalyst/hr) | 100–10,000 | 100–10,000 |
| Stirrer speed (rpm) | — | 600–4000 |
| Recycle gases | $C_4^-/CH_4/CO_2$ | $C_4^-/CH_4/CO_2$ |
| Diluent gases | $N_2/Ar/CH_4/$ light hydro- carbons/$CO_2$ | $N_2/Ar/CH_4/$light hydrocarbons/$CO_2$ |

A magnetically stabilized fluidized bed as is described in U.S. Pat. No. 4,115,927 is also suitable for this reaction.

Having thus described the invention, the following are examples which illustrate the various workings of it. They are not intended to limit the invention in any way.

EXAMPLE 1

The base catalyst was prepared in a high surface area, low excess carbon form by a gas phase pyrolytic decomposition reaction driven by a cw $CO_2$ laser. The reactants were $Fe(CO)_5$ and $C_2H_4$. The $C_2H_4$ also served to absorb energy from the laser beam, allowing rapid heating of the reactants to reaction temperature. Post-reaction quenching is also very rapid, preventing extensive decomposition of the $C_2H_4$ on the catalyst particles and thus minimizing excess carbon content of the solid.

The reactor is shown in FIG. 1. It was constructed around a mini-flange 6-way cross. As shown in the FIGURE, the vertical axis of the apparatus was used for introduction of the reactants and take-off of products. One horizontal axis was used for passage of the laser beam, while the remaining horizontal axis was used for monitoring the reaction. Argon inlets were provided near each of the four windows to prevent deposition of particulates on the windows. The $C_2H_4/Fe(CO)_5$ mixture entered the cell through a tube which was concentric with a slightly larger tube to a point 1–4 mm below the laser beam. The outer tube was used to provide an argon stream surrounding the reactant stream, thereby promoting stable flow of the reactants into the laser beam.

The laser was operated in a cw mode on the 10P(20) line at 944 cm$^{-1}$. Although not resonant with the 950 cm$^{-1}$ Q-branch of $C_2H_4$, this line is absorbed strongly enough by weaker $C_2H_4$ absorption bands to drive the pyrolytic reaction. The laser produced about 150 W in a beam focused to 6 mm diameter at the reaction zone, yielding a flux of 500 W/cm$^2$.

The synthesis was conducted at a reactor pressure of about 300 torr. The total argon flow to the four cell windows was about 70 SCCM (cc/min @ STP), while the argon flow coaxial to the reactants was also 70 SCCM. The $C_2H_4/Fe(CO)_5$ mixture was provided by bubbling $C_2H_4$ through liquid $Fe(CO)_5$ held at ambient temperature (23° C.) where the vapor pressure is 25 torr. [Gilbert, A. G.; Sulzmann, K. G. P., *J. Electrochem. Soc.* 1974, 121, 832–834.] The $C_2H_4$ flow rate was about 6 SCCM. Since the $Fe(CO)_5$ will essentially attain its equilibrium vapor pressure in the $C_2H_4$ stream under these flow conditions, the ratio of the reactants in the gas stream is determined by the total reactor pressure; $C_2H_4:Fe(CO)_5=(300-25):25=11:1$.

The laser-driven reaction gave a bright yellow flame, indicating that quite high temperatures were obtained. Under the flow and pressure conditions given above, the residence time of the reactants in the laser beam is 25–40 ms and the quenching rate should be fast enough to keep the total time at high temperature, e.g., above about 500° C., to 0.1 s or less.

The solid products were collected on an 0.5 μm-pore Teflon membrane filter. The gaseous products were monitored by gas chromatograph (gc) and infrared detector (ir). The ir showed that conversion of Fe(CO)$_5$ to products was quantitative under reaction conditions. The characteristic γ (CO) bands of Fe(CO)$_5$ could not be seen in the product gases, though free CO was present. The GC showed that most of the C$_2$H$_4$ did not react. The gas yields were to some extent dependent upon the linear flow rate of the reactant stream at the laser beam as shown below. Since the reactant stream does undergo some spreading as it enters the reactor, the linear velocity decreases with distance from the inlet tip. Raising the laser beam further above the inlet tip, or alternatively, decreasing the flow rate of the reactants, led to increased residence time of the reactants in the beam. The gas yields then indicated higher reaction temperature, or a longer reaction, or both, as demonstrated by the increase in yields of C$_2$H$_2$ and CH$_4$ relative to C$_2$H$_4$.

|  | Measured Mole %, TCD | |
| --- | --- | --- |
| Gas | High Flow | Low Flow |
| C$_2$H$_4$ | 64 | 57% |
| CO | 32 | 29% |
| C$_2$H$_2$ | 3.3 | 12.5% |
| CO$_2$ | 0.67 | 0.08% |
| CH$_4$ | 0.50 | 1.55% |

H$_2$ was also observed, but the peak area is not meaningful (He carrier). A peak for C$_2$H$_6$ could be observed by eye in the GC trace, but was so weak and broad that the integrator normally did not detect it. The yield was measured at 0.06% of the gases in one instance.

The analysis of one sample of solid prepared by the above method was: Fe, 86.2%; C, 12.74%; O, 1.73%; H, <0.35%. X-ray diffraction showed that the major phase present was Fe$_3$C. The BET surface area was 27 m$^2$/g, and XPS showed that the surface was carbon rich, with only Fe and C present. The catalyst so prepared was not pyrophoric and did not appear to oxidize significantly in air. Analysis by Mössbauer spectroscopy showed that Fe$_3$C was the major phase, with smaller amounts of α-Fe and γ-Fe also present.

EXAMPLE II

A laser generated Fe/C catalyst made according to Example I with about 5–15% wt. of amorphous carbon was impregnated with K$_2$CO$_3$ to yield a material containing about 2% wt. K. This material was examined in a continuously stirred tank reactor at reaction conditions of 270° C., 2/1 H$_2$/CO, 4000 V/V cat/hr, 75 psig, octacosane, 600 rpm. The results are shown below:

| % CO conversion | 66.5 |
| --- | --- |
| Wt. % selectivity (CO$_2$ free basis) | |
| CH$_4$ | 5.6 |
| C$_2$° | nil |
| C$_2$= | 3.7 |
| C$_3$° | 0.5 |
| C$_3$= | 4.3 |
| C$_4$° | 0.3 |
| C$_4$= | 3.5 |
| C$_5$+ | 82.1 |
| % olefin in C$_2$–C$_4$ | 93.5 |

The results demonstrate the high olefin selectivity provided by the alkali promoted catalyst of our invention.

EXAMPLE III

A mixture of 2.0 g of the laser generated Fe/C powder and 6 g of MgO were pelletized, crushed, and sieved (80–150 Tyler mesh) and examimed in a down flow fixed-bed reactor at 221° C., 2/1 H$_2$/CO, 3000 V/V/hr, and 75 psig.

| % CO conversion | 45.7 |
| --- | --- |
| to CO$_2$ | 9.0 |
| to Hydrocarbons | 36.7 |
| Wt. % selectivity (CO$_2$ free basis) | |
| CH$_4$ | 5.0 |
| C$_2$–C$_4$ | 9.0 |
| C$_5$+ | 86.0 |
| C$_2$=/C$_2$° | 0.7 |
| C$_3$=/C$_3$° | 4.0 |

The results dimonstrate the usefulness of the laser generated catalyst in the synthesis of C$_5$+ hydrocarbons.

EXAMPLE IV

A 300 cc Parr Continuously Stirred Tank Reactor (CSTR) was charged with 8.0 g of a conventionally prepared catalyst Fe$_{4.75}$Co$_{0.25}$C$_2$/x g atom % K where x=0, 2 and 10. The material contains an additional carbon phase, ca. 50–70% wt. The reactor was attentively charged with 2.0 g of a laser generated carbide catalyst Fe$_3$C$_y$/x g atom % K where y is from 1 to 2 and x=0 or 2.0. A slurry medium consisting of 70 g of octacosane C$_{28}$H$_{58}$ containing trace levels of sodium bromide, ≦300 ppm, was also charged, the system purged with a gas mixture H$_2$:CO:N$_2$, 60:30:10 molar ratio and then brought to reaction conditions: 240° C., 75 psi, 60:30:10 sccm H$_2$:CO:N$_2$, with stirring at 600 rpm. An exit gas analyzer was employed to determine the extent of CO hydrogenation, the carbon efficiency to CH$_4$ and the olefin content of the C$_2$–C$_4$ fraction. Higher molecular weight products were analyzed off-line on completion of the experiment. Results are provided in the Table below. The high volumetric activity and good olefin selectivity of the laser generated catalyst, even with 0% K are clearly shown.

The laser generated catalyst with about 2% K was found to provide unusually high selectivity for production of hydrocarbon wax even when compared to the Fe-Co analog with 10% K.

TABLE

| | FeCoC cat. % olefin in | | | | FeC cat. % olefin in | | | |
| --- | --- | --- | --- | --- | --- | --- | --- | --- |
| % K | % conv | C$_2$–C$_4$ | % CH$_4$ | % C$_5$+ | % conv | C$_2$–C$_4$ | % CH$_4$ | C$_5$+ |
| 0 | 72 | 37 | 20 | 40 | 55 | 86 | 7 | 78 |
| 2 | 48 | 80 | 10 | 64 | 38 | 87 | 5 | 88 |
| 10 | 40 | 87 | 10 | 64 | — | — | — | — |

We claim as our invention:

1. A composition of matter comprising finely divided non-pyrophoric iron-carbon catalytic particles comprising iron and carbon in the substantial absence of silicon, a substantial portion of which is cementite, produced in a reaction zone in the presence of laser radiation under such conditions of laser flux density, power adsorption, concentration of iron compound reactants selected from the group consisting of iron carbonyls, iron acetylacetonate, and ferrocene, and pressure sufficient to produce non-pyrophoric iron-carbon particles having average diameters between 1 and 100 nm, and which particles are subsequently impregnated with at least 2% of a promoter selected from the group of the salts and oxides of alkali and alkaline earth metals.

2. The composition of claim 1 wherein at least a portion of the iron is in the $\alpha$ and $\gamma$ phase.

3. The composition of claim 1 wherein the particles contain at least some free carbon.

4. The composition of claim 3 wherein at least some of said free carbon is situated on the particles' surface.

5. The composition of claim 1 wherein said average diameters are between 10 and 50 nm.

6. The composition of claim 1 wherein said iron compound is $Fe(CO)_5$.

7. The composition of claim 1 wherein said at least one promoter comprises between 2 and 10% by weight of the catalyst alkali and alkaline metals.

8. The composition of clam 7 wherein said promoter comprises the salts and oxides of potassium.

9. The composition of claim 7 wherein said promoter comprises the salts and oxides of magnesium.

10. The composition of claim 1 wherein said particles are supported on a refractory support.

11. The composition of claim 6 wherein the particles are supported on refractory support.

12. The composition of claim 7 wherein the particles are supported on a refractary support.

* * * * *